United States Patent [19]
Bond et al.

[11] Patent Number: 5,922,920
[45] Date of Patent: Jul. 13, 1999

[54] CATALYTIC PRODUCTION OF ARYL ALKYL HYDROPEROXIDES BY POLYNUCLEAR TRANSITION METAL AGGREGATES

[75] Inventors: Jeffrey Evans Bond, Flemington, N.J.; Sergiu Mircea Gorun, Providence, R.I.; George William Schriver, Somerville, N.J.; Robert Timothy Stibrany, Long Valley, N.J.; Thomas Henry Vanderspurt, Stockton, N.J.; Grayson Hall Via, Westfield, N.J.; Baoshan Zhang, Upton, N.Y.; Jihad Mohammed Dakka, Kessel-lo, Belgium

[73] Assignee: Exxon Chemical Patents Inc., Houston, Tex.

[21] Appl. No.: 08/626,739

[22] Filed: Apr. 2, 1996

Related U.S. Application Data

[63] Continuation-in-part of application No. 08/402,077, Mar. 10, 1995, Pat. No. 5,504,256.

[51] Int. Cl.⁶ .............. C07C 45/00; C07F 13/00
[52] U.S. Cl. .............. 568/342; 556/28; 556/45; 556/49; 556/50; 568/569; 568/573; 568/574; 568/575; 568/430; 568/798
[58] Field of Search .............. 556/28, 45, 49, 556/50; 568/569, 573, 574, 575, 798, 430, 342

[56] References Cited

U.S. PATENT DOCUMENTS

| | | | |
|---|---|---|---|
| 2,954,405 | 9/1960 | Hock et al. | 260/610 |
| 4,013,725 | 3/1977 | Yoneitsu et al. | 260/610 B |
| 5,025,101 | 6/1991 | Gorun et al. | 556/50 |
| 5,041,575 | 8/1991 | Gorun et al. | 556/28 |
| 5,183,945 | 2/1993 | Stibrany et al. | 568/574 |
| 5,504,256 | 4/1996 | Bond et al. | 568/575 |

OTHER PUBLICATIONS

K. Wieghardt, *Angew. Chem. Int. Ed. English*, 28, p. 1153 (1989).
J. B. Vincent, G. Chistou, *Adv. Inorg. Chem.*, 33, p. 197, (1989).
G. Christou, *Acc.Chem. Respectfully.*, 22, p. 328 (1989).
G. W. Brudvig, R. H. Crabtree, *Prog. Inorg. Chem.*, 37, p. 99 (1989).

*Primary Examiner*—Porfirio Nazario-Gonzalez
*Attorney, Agent, or Firm*—John F. Hunt

[57] ABSTRACT

A method is provided for preparing organic hydroperoxides by oxidizing aryl alkyl hydrocarbons having a benzylic hydrogen with an oxygen containing gas using as a catalyst an oxo (hydroxo) bridged tetranuclear metal complex having a mixed metal core, one metal of the core being a divalent metal selected from Zn, Cu Fe, Co, Ni, Mn or mixtures thereof and another metal being a trivalent metal selected from In, Fe, Mn, Ga, and Al. A method is also provided for the manufacture of the catalyst

1 Claim, 3 Drawing Sheets

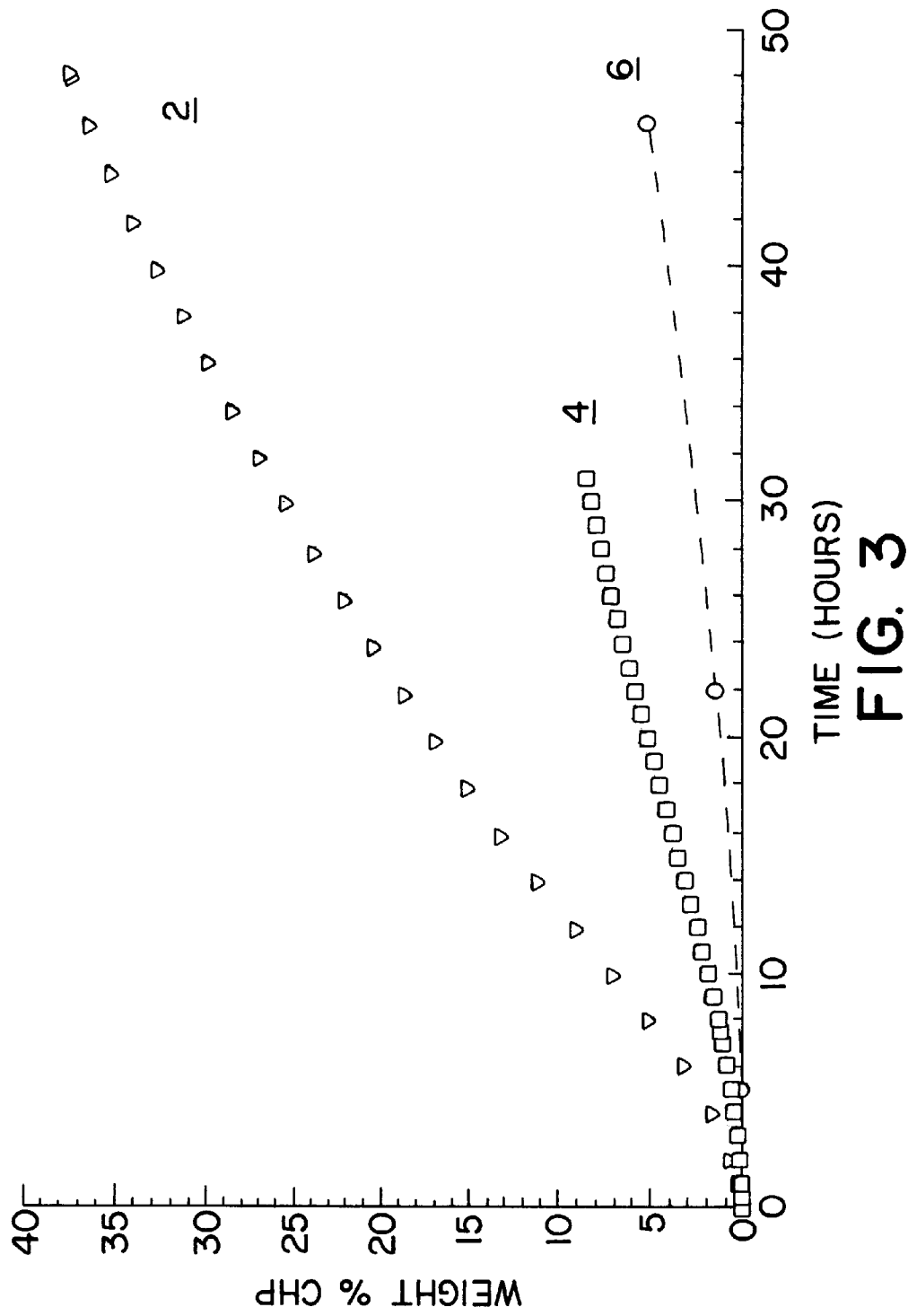

CATALYTIC PRODUCTION OF ARYL ALKYL HYDROPEROXIDES BY POLYNUCLEAR TRANSITION METAL AGGREGATES

This application is a Continuation-In-Part of Ser. No. 08/402,077 filed on Mar. 10, 1995, now U.S. Pat. No. 5,504,256.

FIELD OF INVENTION

This invention relates to a new class of compounds. More specifically, it relates to compounds having an oxo (hydroxo) bridged tetranuclear, mixed metal core and to their method of preparation and use in catalysing the oxidation of aryl alkyl hydrocarbons in the presence of an oxygen-containing gas to produce aryl alkyl hydroperoxides.

BACKGROUND OF THE INVENTION

For information on the plethora of known oxo bridged tetranuclear metal compounds, reference is made to the following review articles: K. Wieghardt, *Angew. Chem.Int. Ed. English*, 28, p. 1153 (1989); J. B. Vincent, G. Christou, *Adv. Inorg. Chem.*, 33, p. 197, (1989); G. Christou, *Acc. Chem. Res.*, 22, p.328 (1989); and G. W. Brudvig, R. H. Crabtree, *Prog. Inorg. Chem.*, 37, p. 99 (1989). These articles describe primarily manganese complexes in which the manganese is present in various oxidation states, spatial arrangements and the like. Other literature references and tetranuclear manganese complexes are referred to and disclosed in U.S. Pat. No. 5,025,101.

Compounds having an oxo (hydroxo) bridged tetranuclear, mixed metal core, however, have not been previously reported. Hence, the ability to prepare such materials is highly desired.

The production of organic hydroperoxides from aryl alkyl hydrocarbons in the presence of various transition metal salt complexes has been described in the literature. See, for example, U.S. Pat. No. 2,954,405 disclosing the production of organic hydroperoxides by autoxidation of hydrocarbons in the presence of molecular oxygen and metal phthalocyanines as catalysts. Similarly, U.S. Pat. No. 4,013,725 discloses a process for preparing hydroperoxides in a homogeneous system by autoxidizing secondary alkyl group-substituted methylbenzenes in the presence of water, a base, an oxygen containing gas, and a water-soluble chelate compound in which multidentate ligands are coordinated to at least one metal from the class of cobalt, nickel, manganese, copper, and iron.

In U.S. Pat. No. 5,025,101 and U.S. Pat. No. 5,183,945 tetranuclear manganese complexes, and their method of preparation, and their use as catalyst in the production of hydroperoxide are disclosed.

In part the present invention is predicated on the discovery that certain compounds having an oxo (hydroxo) bridged tetranuclear, mixed metal core, are useful as oxidation catalysts, in the presence of oxygen containing gas, for the production of organic hydroperoxides.

SUMMARY OF THE INVENTION

Accordingly, in one embodiment, the present invention comprises a composition of matter having the formula:

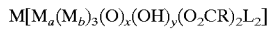

wherein M is an ammonium ion, one or more alkali metal ions, one or more alkaline earth metal ions, or mixtures thereof. M may thus be a single ion or a mixture of ions of differing valence; Ma is a divalent metal or mixture of divalent metals, Mb is trivalent metal or mixture of trivalent metals; x and y are numerical values the sum of which equals 2. The exact number of ions M and their valence will depend on the value of y and x and the consequential negative valence (n−) of the complex anion $[M_a(M_b)3(O)_x(OH)_y(O2CR)2L2]^{n-}$. When y=x=1 the negative valence of the complex anion will be 4− and M may therefore be four ammonium or alkali metal ions or mixtures thereof, or may be two alkaline earth metal ions or may be two ammonium or alkali metal ions or mixtures thereof and one alkaline earth metal ion. When y=2 and x=0 the negative valence of the complex anion is 3−, when y=0 and x=2 the negative valence of the complex anion is 5−, and there are various combinations of cations which may be used to form an electrically neutral material with such valences. R is hydrogen or a hydrocarbyl group; and L is a ligand having the formula:

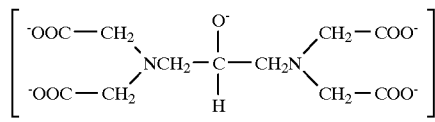

In a further embodiment the present invention comprises a method of preparing compounds having the formula:

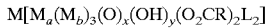

wherein M, L, $M_a$, $M_b$, x, y and R are as listed above. The method comprises forming an aqueous solution containing: (a) a compound having the formula:

(compound I)

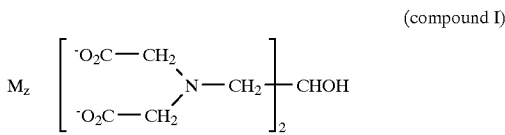

wherein M consists of ammonium, alkaline, or an alkaline earth metal ions or mixtures thereof in sufficient amounts for compound I to be electrically neutral, (b) a mixture of a water soluble salt of at least one divalent metal $M_a$ and a trivalent metal $M_b$; and (c) a source of a carboxylate, $RCO_2-$, where R is hydrogen or a hydrocarbyl group whereby a compound having the formula $M[M_a(M_b)_3(O)_x(OH)_y(O_2CR)L_2]$ is prepared. In one embodiment, the solution is formed in situ by adding an oxidant, such as air, oxygen or hydrogen peroxide to an aqueous solution of compound I, a carboxylate source and (i) a water soluble salt of a divalent metal Ma and a metal oxidizable to a trivalent metal, $M_b$, or (ii) a water soluble salt of a divalent metal oxidizable to a trivalent metal, $M_b$, the addition being in an amount and for a time sufficient to oxidize at least part of oxidizable divalent metal to the trivalent metal $M_b$.

The compounds of the present invention, in which at least one of $M_a$ and $M_b$ is selected from a metal have an incomplete d electronic shell, having particular suitability for use in oxidation of hydrocarbons as peroxide decomposers. Other compounds of the present invention form solid solutions with the former thereby serving as a diluent and catalyst support for the former compounds.

The present invention further provides a method for preparing organic hydroperoxides, which method comprises contacting an aryl alkyl hydrocarbon having a benzylic hydrogen with an oxygen containing gas in the presence of an oxo (hydroxo) bridged tetranuclear metal complex having a mixed metal core, one metal of the core being a divalent metal selected from Zn, Cu, Fe, Co, Ni, Mn or mixtures thereof and another metal being a trivalent metal selected from In, Fe, Mn, Ga and Al.

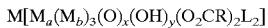

in which $x=y=1$, $M_b=Mn$ and $M_a=$a mixture of Mn and Cu.

Figure 1:
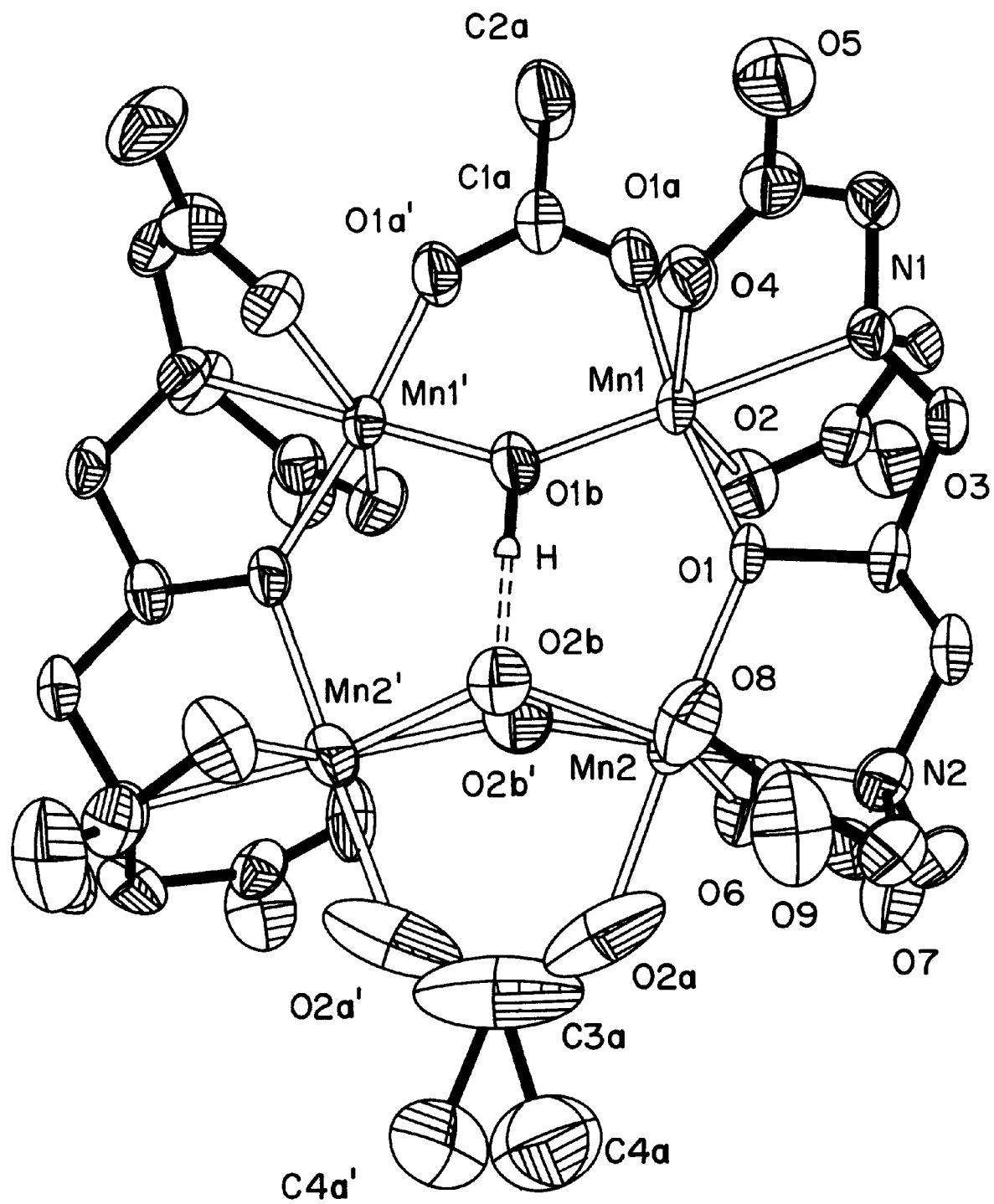
FIG. 1 in the instant application illustrates the oxo (hydroxo) bridged tetranuclear metal core for the composition
Figure 2:
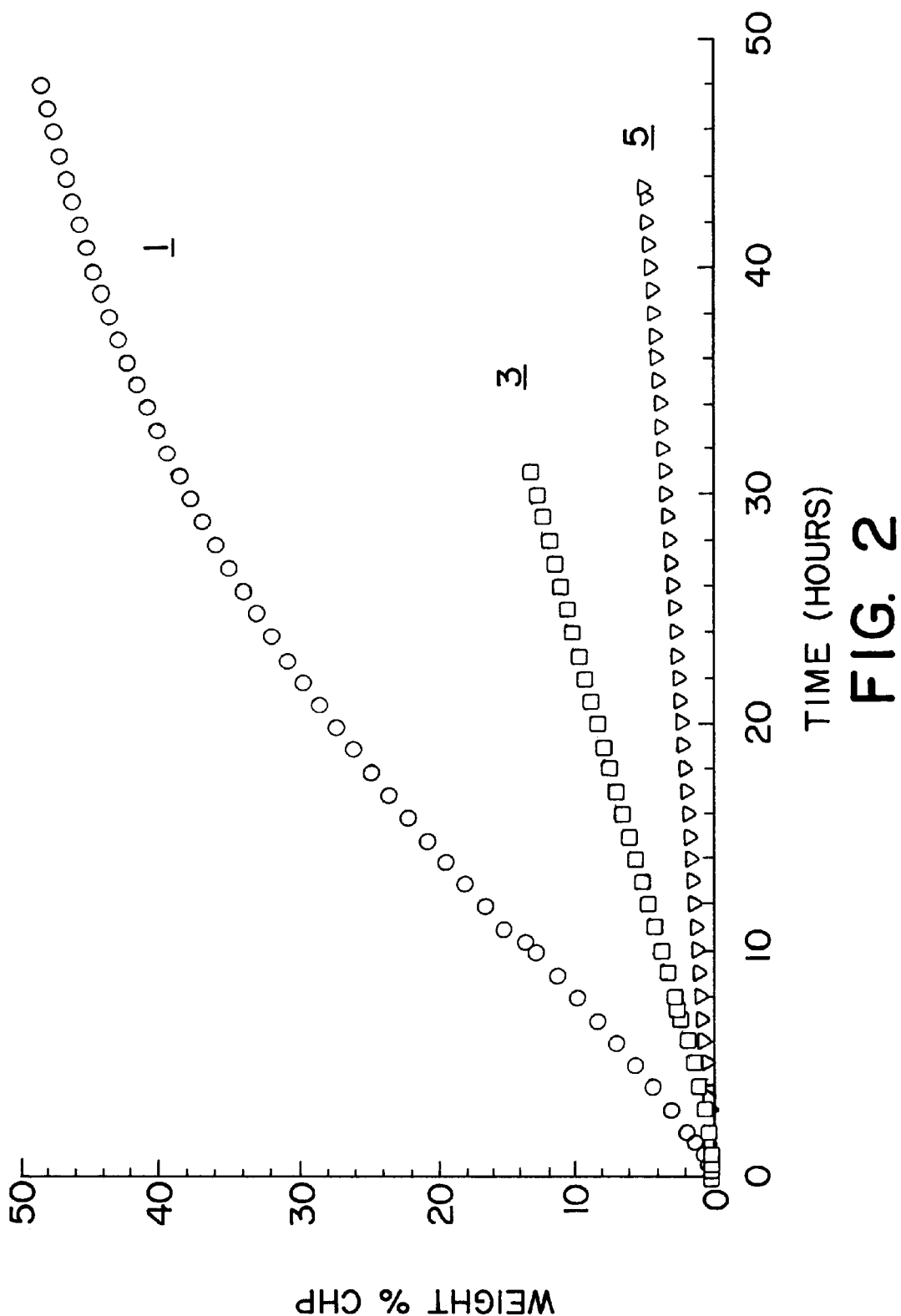

FIGS. 2 and 3 show the weight percent of cumene hydroperoxide produced from cumene in the presence of and various catalysts by the oxidation process of the present invention. Also shown in FIG. 3 is the amount of cumene hydroperoxide produced in the presence of cumene, air and cumene hydroperoxide as initiator.

DETAILED DESCRIPTION OF THE INVENTION

The compounds of the present invention have the formula:

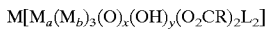

wherein M is an ammonium ion, one or more alkali metal ions, one or more alkaline earth metal ions, or mixtures thereof, preferably Li, Na, K, $NH_4$, Mg, Ca, Sr, Ba or mixtures thereof. R is hydrogen or a hydrocarbyl group especially alkyl, aryl, and aralkyl groups. Preferably R is an alkyl group having from 1 to about 30 carbon atoms and, more preferably, R has from 1 to about 10 carbon atoms; and when R is an aralkyl group, it preferably has from 7 to 10 carbon atoms. $M_a$ is a divalent metal like Zn, Cu, Fe, Co, Ni, Mn; and, $M_b$ is a trivalent metal like In, Fe, Mn, Ga, Al. The subscripts x and y are numerical values the sum of which is 2; and L is a ligand having the formula:

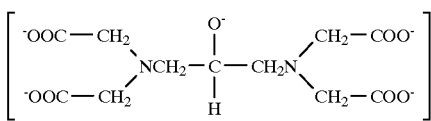

As shown in the accompanying figure, these novel compounds have a core structure of four metal atoms which are bridged by oxo and hydroxo groups and, hence, these compounds are referred to as oxo(hydroxo) bridged tetranuclear metal compounds.

In the process for the preparation of compounds of the present invention exemplary salts of $M_a$ and $M_b$ include metal chlorides, bromides, nitrates, tetrafluoroborates, and sulfates, provided, however, that sulfates are not used when M is Ca, Ba or Sr. Exemplary sources of carboxylate include carboxylic acids and alkaline metal salts of carboxylic acids. Among suitable aqueous containing solutions are water, water-alcohol, and water-dimethyl fromamide mixtures. In general it is particularly preferred to use water as the solvent.

The molar ratio of compound I to the metal salts containing $M_a$ and $M_b$ generally will be in the range of from about 1:1 to about 1:3 and preferably about 1:2.

Because the acid analogue of the ligand L is commercially available, it is particularly preferred in the practice of the present invention to prepare an aqueous containing solution of compound I by first neutralizing an aqueous solution of its conjugated acid with an alkali or alkaline earth metal hydroxide or mixture thereof, and thereafter adding the metal carboxylates or metal salts and source of carboxylate.

In one embodiment, the solution is formed in situ by adding an oxidant, such as air, oxygen or hydrogen peroxide to an aqueous solution of compound I, a carboxylate source and (i) a water soluble salt of a divalent metal $M_a$ and a metal oxidizable to a trivalent metal, $M_b$, or (ii) a water soluble salt of a divalent metal oxidizable to a trivalent metal, $M_b$, the addition being in an amount and for a time sufficient to oxidize at least part of the oxidizable divalent metal to the trivalent metal $M_b$.

As pointed out above, this aqueous mixture is then oxidized if needed. The need for oxidation arises only when $M_b$ is not present in its trivalent state to start with. As shown later in Preparations 11 and 12, for the preparation of the complex in which $M_a$ is Mn and $M_b$ is Ga, there is no need for oxidation because Ga is already present as Ga(III). On the other hand, as shown in Preparations 8, 9 and 10 for the preparation of the complex in which $M_a$ in Zn and $M_b$ is Mn, one may start with Mn(II) salts and oxidize the Mn(II) to the required Mn(III) state. This is achieved by adding an oxidant such as air, molecular oxygen, or hydrogen peroxide. When air or oxygen is employed, the gas is bubbled through the mixture at temperatures in the range of about 20° C. to about 60° C. and in an amount sufficient to form the desired compound. When hydrogen peroxide is used as the oxidant, in general the peroxide will have a concentration range of about 10 wt % to 30 wt % and, preferably, about 25 wt % and will be used in excess, for example, up to about 10 times the stoichiometric amount required. The addition of hydrogen peroxide to the reaction mixture results in an exothermic reaction and consequently it is particularly preferred to maintain the temperature of the reaction mixture during oxidation in the range of about 10° C. to 60° C., and preferably, in the range of about 20° C. to 40° C.

Typically, the desired compound is recovered by fractional crystallization from suitable solvents such as water-dimethylformamide mixtures.

The compounds of the present invention have utility as catalysts for the production of aryl alkyl hydroperoxides. For example following the procedure set forth in U.S. Pat. No. 5,183,945 which is incorporated herein by reference, the compounds of the invention, in which at least one of $M_a$ and $M_b$ is a metal having an incomplete d electronic shell, may be used to catalyse the oxidation of cumene to cumene hydroperoxide.

The oxidation process of the present invention is therefor carried out by contacting an aryl alkyl hydrocarbon with an oxygen-containing gas and at least one tertiary alkyl hydroperoxide and a catalytically effective amount of either an oxo (hydroxo) bridged tetranuclear metal complex having a mixed metal core.

The aryl alkyl hydrocarbons employed as starting materials in this process may be obtained from commercial sources. Preferably the aryl alkyl hydrocarbons will have a melting point within the range of temperatures at which the process of the present invention is operated or be capable of being solubilized in an inert solvent. Importantly, the aryl alkyl hydrocarbons should contain a benzylic hydrogen. An example of useful aryl alkyl hydrocarbons is represented by the general formula:

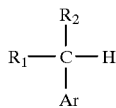

where $R_1$ and $R_2$ may be the same or different organo groups, preferably alkyl groups having from 1 to about 10 carbon atoms, or hydrogen and Ar is an aromatic or substituted aromatic group, such as alkyl and halo, substitute aromatic groups. $R_1$ and $R_2$ may most preferably be bonded together to form a cycloaliphatic group such as, for example, a cyclohexyl group in which case the aryl alkyl hydrocarbon will be cyclohexylbenzene. In the case of alkyl substituted aromatic groups, the alkyl group generally will have from 1 to about 10 carbon atoms.

The oxygen containing gas used preferably is air or oxygen, and, more preferably, is air.

The amount of catalyst used will vary depending upon the nature and amount of the organic starting material to be oxidized. In general from about 0.001 to about 0.5 parts by weight of catalyst per 100 parts of substrate and preferably from about 0.1 to about 0.2 parts per 100 parts of substrate are satisfactory.

In the process of the present invention, the solvent for the reaction is preferably an excess amount of the aryl alkyl hydrocarbon to be oxidized, e.g. cyclohexyl benzene; however, hydrocarbons such as benzene, chlorobenzene, halogenated hydrocarbons, and the like may be employed as solvents.

Preferably the hydrocarbon, catalyst and oxygen or oxygen containing gas are contacted in such a way as to provide for good mixing, such as rapid bubbling of the gas through the mixture or mechanical agitation. Preferably air is used in the contacting.

The flow rate of air is not critical and the optimum rate will vary depending on the reaction temperature and pressure employed. In the case of the oxidation of cumene to cumene hydroperoxide, for example, the flow rate of air preferably will be at least 2 liters/hr up to about 10 liters/hr per 100 g of cumene.

The reaction temperature may range from about 0° C. to about 90° C., preferably from about 60° C. to about 80° C. Temperatures at the lower end of the preferred range are more desirable.

Typically the contacting is conducted at atmospheric pressure. Importantly, the present invention results in the selection oxygenation of the aryl alkyl hydrocarbon and does not oxygenate the aromatic or aliphatic hydrocarbons present in the starting material.

In conducting the method of this invention, the formation of the corresponding organic hydroperoxide can be monitored, for example, by analyzing aliquots by NMR, iodometric titration, chromatography or other means readily known to one skilled in the art. Also, the organic hydroperoxide is readily recovered from the reaction mixture by conventional methods, for example distillation, and as a result, the process may be run in batch or continuously. In a continuous process, the aryl alkyl hydrocarbon starting material may be passed over the catalyst in a bed or otherwise contacted with the catalyst. The organic hydroperoxide may be withdrawn and the organic starting material recycled.

The present invention further provides a process for the manufacture of phenol and cyclohexanone from cyclohexyl benzene which process comprises;

(a) contacting cyclohexyl benzene with an oxygen-containing gas and an oxo(hydroxo) bridged tetranuclear metal complex having mixed metal core, under catalytic oxidation conditions to form cyclohexylbenzene hydroperoxide and (b) decomposing the cyclohexylbenzene hydroperoxide to form a mixture comprising phenol and cyclohexanone.

Preferably the cyclohexylbenzene hydroperoxide is decomposed with acid.

The invention will now further be described by means of the following examples.

EXAMPLES

A. Catalyst Preparation:

A series of detailed catalyst preparations are provided herein to illustrate the general preparation techniques previously described. In the preparations which follow, DHPTA refers to 1,3-diamino-2-hydroxypropane-N, N, N'N'-tetraacetic acid; DMF is dimethylformamide; MeOH is methyl alcohol. Also, in those preparations in which the subscript s is used in the formula, s is a value greater than zero but less than 1, depending upon the ratio of mixed divalent metals used.

Preparation 1

Preparation of $Ba_2[(Cu_{0.4}Mn_{0.6})Mn_3(O)(OH)(O_2CCH_3)_2L_2]$

In a 50 ml Erlenmeyer flask, 268 mg of DHPTA was added to ~7 ml $H_2O$. Then enough $Ba(OH)_2.H_2O$ was added to give a clear solution, followed by 93 mg of $Cu(O_2CCH_3)_2.H_2O$ and 343 mg of $Mn(O_2CCH_3)_2.4H_2O$. About ½ ml of MeOH and ~1 ml of DMF was added next, while stirring. After the pH was brought to ~8 by adding slowly $Ba(OH)_2$, the solution was treated with ~1 ml of ~25% $H_2O_2$. During this addition, the solution color changed from blue to brown. This filtered solution gave crystals by evaporation. The structure of the product was determined by simple crystal x-ray diffraction and sorption spectroscopy. The simple crystal x-ray analysis revealed the presence of CU(II) ions which selectively replaced the Mn(II) ions.

Preparation 2

Preparation of $Ca_2[(Cu_sMn_{1-s})Mn_3(O)(OH)(O_2CCH_3)_2L_2]$

The procedure of Preparation 1 was followed except that $Ca(OH)_2$ was used in place of $Ba(OH)_2$.

Preparation 3

Preparation of $Ba_2[CuFe_3(O)(OH)(O_2CCH_3)_2L_2]$

In a 50 ml Erlenmeyer flask, 268 mg of DHPTA and 100 μl of 100% $CH_3COOH$ was added to ~8 ml $H_2O$. The pH was brought to ~6 with $Ba(OH)_2.H_2O$. Then 110 mg of $Cu(O_2CCH_3)_2.4H_2O$ and 3 45 mg of $Fe(NO_3)_3.6H_2O$ was added to the solution. Then the pH was brought to ~7.5 with $Ba(OH)_2.H_2O$ and 1 ml DMF was added. The yellow green solution was filtered and the product crystallized by evaporation.

Preparation 4

Alternate Preparation of $Ba_2[CuFe_3(O)(OH)(O_2CCH_3)_2L_2]$

In a 50 ml Erlenmeyer flask, 268 mg of DHPTA was added to 10 ml $H_2O$. The solution was brought to pH ~6 with $Ba(OH)_2.H_2O$. Then 105 mg of $Cu(O_2CCH_3)_2.4H_2O$ and 540 mg of $Fe(␣C10_4)_3.6H_2O$ and 100 μl of $CH_3COOH$ were all added. After stirring, the pH was brought to 7.5–8.0 with $Ba(OH)_2$ and 1 ml DMF was added. The crystalline product was obtained by evaporation.

Preparation 5
Preparation of $Ca_2[ZnGa_3(O)(OH)(O_2CCH_3)_2L_2]$ 268 mg of DHPTA was added to about 8 ml $H_2O$ then brought to pH 6 using $Ca(OH)_2$. Then 115 mg of $Zn(O_2CCH_3).2H_2O$ and 320 mg of $Ga(NO_3)_3.6H_2O$ and 100 µl glacial acetic acid was added to the solution. The pH was then brought to about 8 with $Ca(OH)_2$ and 2 ml of DMF was added. The solution was filtered and the product was obtained by crystallization.

Preparation 6
Preparation of $Ba_2[ZnGa_3(O)(OH)(O_2CCH_3)_2L_2]$

In a 50 ml Erlenmeyer flask, 268 mg of DHPTA was added to ~8 ml $H_2O$. The solution was brought to pH 6 with $Ba(OH)_2.H_2O$. Then 120 mg of $Zn(O_2CCH_3)_2.2H_2O$ and 330 mg of $Ga(NO_3)_3.6H_2O$ was added while stirring. The pH was brought to 7.5 with $Ba(OH)_2.H_2O$. Following the addition of 1 ml of DMF, the solution was filtered and the product crystallized by evaporation.

Preparation 7
Preparation of $Na_4[ZnGa_3(O)(OH)(O_2CCH_3)_2L_2]$

In a 50 ml Erlenmeyer flask 268 mg of DHPTA was added to ~6 ml $H_2O$. The solution was brought to pH ~6.0 with NaOH. Then three drops of 100% $CH_3COOH$ was added, followed by 105 mg $Zn(O_2CCH_3)_2.2H_2O$ and 340 mg of $Ga(NO_3)_3.6H_2O$. The pH was then brought to ~8 using NaOH, the solution was filtered and 1 ml DMF added. The product was obtained by crystallization.

Preparation 8
Preparation of $Ca_2[(Zn_sMn_{1-s})Mn_3(O)(OH)(O_2CCH_3)_2L_2]$ 268 mg of DHPTA was added with 10 ml $H_2O$ to a 50 ml flask. The solution was brought to pH 8 with powdered $Ca(OH)_2$. In another flask, 330 mg of $Mn(O_2CCH_3)_2.4H_2O$ and 105 mg $Zn(O_2CCH_3)_2.2H_2O$ was dissolved in 10 ml of 1:1 $H_2O$: MeOH. Then 200 mg of $CaCl_2$ was also dissolved in the $(Zn,Mn)(O_2CCH_3)_2$ solution. Next, the Mn/Zn containing solution was added to the DHPTA solution and stirred for 5 minutes. The pH was adjusted to 8.0 with $Ca(OH)_2$, after which ½ ml of 30% $H_2O_2$ was added dropwise. Finally, 4 ml of DMF was added, the solution was filtered and the product was obtained by crystallization.

Preparation 9
Alternative preparation of $Ca_2[(Zn_sMn_{1-s})Mn_3(O)(OH)(O_2CCH_3)_2L_2]$ In a 50 ml Erlenmeyer flask 268 mg of DHPTA was added to ~7 ml $H_2O$. The solution was brought to pH ~6.5 with $Ca(OH)_2$. Then 105 mg at $Zn(O_2CCH_3)_2.2H_2O$ and 330 mg of $Mn(O_2CCH_3)_2.6H_2O$ was added to the solution. The pH was brought to ~8 with $Ca(OH)_2$ and 0.5 ml of ~30% $H_2O_2$ was added giving off heat and gas. 1 ml of DMF was then added. The crystalline product was obtained by evaporation.

Preparation 10
Preparation of $Ba_2[(Zn_sMn_{1-s})Mn_3(O)(OH)(O_2CCH_3)_2L_2]$ In a 50 ml Erlenmeyer flask containing 5 ml $H_2O$, 100 mg of $Ba(OH)_2.H_2O$ was neutralized with concentrated HCl to pH 7. Then 330 mg of $Mn(O_2CCH_3)_2.4H_2O$ and 105 mg $Zn(O_2CCH_3)_2.2H_2O$ were added, along with 10 ml of 1:1 $H_2O$/MeOH. In another 50 ml flask, 268 mg of DHPTA was added to 10 ml of $H_2O$. This was neutralized with solid $Ba(OH)_2$ while stirring. The two solutions were mixed together and stirred for about 10 minutes, after which the pH was adjusted to 8.0 with solid $Ba(OH)_2.H_2O$. Next, 0.5 ml of 30% $H_2O_2$ was added dropwise. Then 5 ml of DMF was added, the solution was stirred 10 minutes and filtered. The product was obtained by crystallization.

Preparation 11
Preparation of $Na_4[MnGa_3(O)(OH)(O_2CCH_3)_2L_2]$

In a 50 ml Erlenmeyer flask, 268 mg of DHPTA was added to ~8 ml $H_2O$ under an Ar blanket. The pH was brought to ~6 with NaOH. Then 100 µl of 100% $CH_3COOH$ was added, followed by 110 mg of $Mn(O_2CCH_3)_2.6H_2O$ and 340 mg of $Ga(NO_3)_3.6H_2O$. The pH was then brought to 8.5 with NaOH. The pale pink crystalline product was obtained via MeOH diffusion in the aqueous solution.

Preparation 12
Preparation of $K_4[MnGa_3(O)(OH)(O_2CCH_3)_2L_2]$

In a 50 ml Erlenmeyer flask, 268 mg of DHPTA was added to ~7 ml $H_2O$. The solution was brought to pH ~6 with KOH. Then 60 µl of 100% $CH_3COOH$ was added, followed by 100 mg of $Mn(O_2CCH_3)_2.6H_2O$ and 350 mg of $Ga(NO_3)_3.6H_2O$. The pH was brought to ~8 with KOH, the solution filtered and layered with MeOH to give pale pink crystalline product.

Preparation 13
Preparation of $Ba_2[(Ni_sMn_{1-s})Mn_3(O)(OH)(O_2CCH_3)_2L_2]$ In a 50 ml Erlenmeyer flask, 268 mg of DHPTA was added to ~8 ml $H_2O$. The pH was brought to ~6.5 with $Ba(OH_2).H_2O$. Next, 110 mg of $Ni(O_2CCH_3)_2.6H_2O$ and 330 mg of $Mn(O_2CCH_3)_2.6H_2O$ were added. The pH was brought to ~8 and then 1 ml $H_2O_2$ (30%) and 1 ml DMF were added slowly. The crystalline product was obtained by evaporation from the filtered solution.

Preparation 14
Preparation of $Ba_2[FeGa_3(O)(OH)(O_2CCH_3)_2L_2]$

In a 50 ml Erlenmeyer flask, 268 mg DHPTA was added to ~7 ml $H_2O$ containing 100 µl of 100% $CH_3COOH$ and the pH was brought to ~6.5 with $Ba(OH)_2.H_2O$. Then 454 mg of $Ga(NO_3)_2.6H_2O$ was added, pH was brought to 8 with $Ba(OH)_2.H_2O$, the solution filtered under argon and $Fe(O_2CCH_3)_2$ was added while stirring. Crystals formed via methanol diffusion.

Preparation 15
Preparation of $K_4[CoMn_3(O)(OH)(O_2CCH_3)_2L_2]$

In a 50 ml Erlenmeyer flask, 268 mg of DHPTA was added to ~10 ml $H_2O$ and the pH was brought to about 6.5 with KOH. Then 110 mg of $CO(O_2CCH_3)_2.4H_2O$ and 320 mg of $Mn(0_2CCH_3)_2.6H_2O$ was added to the solution. The pH was brought to ~8 with KOH and ~2 ml of 30% $H_2O_2$ was added dropwise giving a dark red-brown solution. Then 2 ml of DMF was added and the solution was filtered. Crystals were obtained by evaporation.

Preparation 16
Preparation of $Ca_2[Fe_4(O)(OH)(O_2CCH_3)_2L_2]$

In a 50 ml Erlenmeyer flask, 268 mg of DHPTA was added to ~8 ml $H_2O$ and the pH was adjusted to ~7.5 with $Ca(OH)_2$. Then 420 mg of $Fe(O_2CCH_3)_2$ was added. Then 1 ml of ~30% $H_2O_2$ was added giving a dark green solution. The pH was readjusted to 8.0 with $Ca(OH)_2$. Following the addition of 1 ml DMF, the solution was filtered and crystallized by evaporation.

Examples 1 to 5

A series of runs were conducted using as catalysts the compounds listed in Table 1 below. In each example, 0.1 g of solid catalyst was added to 50 g of neat cumene in a flask. Air at 1 atm of pressure, ws bubbled through the reaction mixture at a rate of 30 ml/min. The temperature of the reaction is maintained at 65° C. The conversion of cumene to cumene hydroperoxide (CHP) was monitored by iodometric titrations and oxygen uptake. The accompanying FIGS. 2 and 3 show the weight % CHP produced vs. time for various catalysts labelled as in Table 1. In FIG. 3, line 6 corresponds to the uncatalyzed auto-oxidation of cumene described in the Comparative Example 1.

TABLE 1

| Example | $M[M_a(M_b)_3(O)_x(OH)_y(O_2CR)_2L_2]$ | | |
|---|---|---|---|
| | M | Ma | Mb |
| 1 | Ba | $Ni_sMn_{1-s}$ | Mn |
| 2 | K | Mn | Ga |
| 3 | Na | Zn | Ga |
| 4 | Ba | Cu | Fe |
| 5 | Ba | Fe | Ga |

Comparative Example 1

12.0 grams of cumene (0.1 mole) was combined with 0.2 cm³ of cumene hydroperoxide (as an initiator) and heated to 100° C. in a oxygen atmosphere with vigorous stirring. In three hours about 3% oxidation to cumene hydroperoxide occurs. Thus the rate observed for the CHP auto catalysed oxidation at 100° C. is about 1% per hour. To compare this with an oxidation carried out at 65° C. a simple extrapolation can be done using the Arrhenius equation. Such as extrapolation indicates a reaction rate of about 0.1% per hour at 65° C. which is one order of magnitude smaller than that obtained with the catalysts of this invention.

We claim:

1. A process for the manufacture of phenol and cyclohexanone from cyclohexyl benzene which process comprises;

(a) contacting cyclohexyl benzene with an oxygen-containing gas and an oxo(hydroxo) bridged tetranuclear metal complex having mixed metal core, under catalytic oxidation conditions to form cyclohexylbenzene hydroperoxide and (b) decomposing the cyclohexylbenzene hydroperoxide to form a mixture comprising phenol and cyclohexanone.

* * * * *